(12) United States Patent
Suzuki et al.

(10) Patent No.: US 11,602,641 B2
(45) Date of Patent: Mar. 14, 2023

(54) LIGHT TREATMENT SYSTEM AND BALLOON CATHETER

(71) Applicant: OLYMPUS CORPORATION, Tokyo (JP)

(72) Inventors: Toshiaki Suzuki, Hino (JP); Takeshi Yamazaki, Hachioji (JP); Koji Matsumoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/188,141

(22) Filed: Mar. 1, 2021

(65) Prior Publication Data
US 2021/0178177 A1 Jun. 17, 2021

Related U.S. Application Data

(63) Continuation of application No. PCT/JP2018/040602, filed on Oct. 31, 2018.

(51) Int. Cl.
*A61N 5/06* (2006.01)
*A61M 25/10* (2013.01)

(52) U.S. Cl.
CPC .......... *A61N 5/0603* (2013.01); *A61M 25/10* (2013.01); *A61M 2025/1065* (2013.01);
(Continued)

(58) Field of Classification Search
CPC .......... A61N 5/0603; A61N 2005/061; A61M 25/10
See application file for complete search history.

(56) References Cited

U.S. PATENT DOCUMENTS

| 4,612,938 A | 9/1986 | Dietrich et al. |
| 2005/0131500 A1 | 6/2005 | Zalesky et al. |

(Continued)

FOREIGN PATENT DOCUMENTS

| JP | S59-095065 A | 5/1984 |
| JP | 02-098373 A | 4/1990 |

(Continued)

OTHER PUBLICATIONS

Tadao Uchibayashi, et al., "Experimental Research on Whole Bladder Wall Photodynamic Therapy Using Scattering Medium", Japanese Journal of Urology, May 1988, vol. 79, No. 5, at pp. 807-813.

(Continued)

*Primary Examiner* — Lynsey C Eiseman
*Assistant Examiner* — Jessica L Mullins
(74) *Attorney, Agent, or Firm* — Scully, Scott, Murphy & Presser, P.C.

(57) ABSTRACT

A light treatment system includes: a probe configured to be inserted into a bladder, the probe including an optical fiber configured to propagate light, and a light emitter that is provided at a distal end of the optical fiber, the light emitter being configured to emit the light; and a balloon catheter into which the probe is inserted, the balloon catheter being configured to be inserted into the bladder, the balloon catheter including a distal end portion that is to be dilated in the bladder, a wall configured to divide inside of the distal end portion into two regions, and a reflector configured to reflect the light emitted by the light emitter, the reflector being provided on a surface of the wall, the surface facing a region of the two regions, the region being where the light emitter is positioned.

5 Claims, 5 Drawing Sheets

(52) U.S. Cl.
    CPC .............. *A61M 2210/1085* (2013.01); *A61N 2005/061* (2013.01); *A61N 2005/063* (2013.01); *A61N 2005/0665* (2013.01)

(56) References Cited

U.S. PATENT DOCUMENTS

| | | | |
|---|---|---|---|
| 2011/0257641 A1* | 10/2011 | Hastings | ................ A61B 18/24 606/15 |
| 2013/0035556 A1* | 2/2013 | Kalser | ............ A61M 25/10185 600/249 |
| 2013/0267885 A1 | 10/2013 | Celermajer et al. | |
| 2016/0213945 A1* | 7/2016 | Burwell | ............. A61K 41/0071 |
| 2019/0269392 A1 | 9/2019 | Celermajer et al. | |

FOREIGN PATENT DOCUMENTS

| | | |
|---|---|---|
| JP | 2007-511286 A | 5/2007 |
| JP | 2017-060825 A | 3/2017 |
| WO | 2005/049127 A1 | 6/2005 |

OTHER PUBLICATIONS

Toshimitsu Misaki, et al., "Photodynamic laser treatment of Bladder Tumors", Acta Urologica Japonica, Dec. 1986, vol. 32, No. 12, at pp. 1941-1948.

International Search Report dated Jan. 8, 2019 received in PCT/JP2018/040602.

\* cited by examiner

LIGHT TREATMENT SYSTEM AND BALLOON CATHETER

CROSS-REFERENCE TO RELATED APPLICATION

This application is a continuation of International Application No. PCT/JP2018/040602, filed on Oct. 31, 2018, the entire contents of which are incorporated herein by reference.

BACKGROUND

1. Technical Field

The present disclosure relates to light treatment systems and balloon catheters.

2. Related Art

Light treatment systems in which treatment is performed using light have been known (see, for example, Japanese Patent Application Laid-open No. S59-095065). This light treatment system includes a sac-like balloon attached to a distal end of a tubular catheter to be inserted into a hollow organ of a human body, such as the bladder. The catheter includes a light conductor, such as optical fiber, inserted therein, and a light emitter at a distal end of the light conductor is placed inside the balloon. The light emitter emits treatment light forward. The balloon is filled with a scattering medium including fat emulsion diluted with a physiological saline solution. Therefore, the treatment light is scattered, and not only the upper part of the bladder, but also the lower part of the bladder is illuminated with the treatment light.

The upper part of the bladder is able to be observed using a rigid endoscope inserted from the urethra. A tumor in the upper part of the bladder is able to be removed by a looped electrosurgical knife, for example. This treatment is called a transurethral resection of a bladder tumor or a TUR-Bt. The lower part of the bladder on the other hand has a prostate around the lower part and is a part where a tumor tends to be generated, but because the lower part is positioned behind the rigid endoscope that has been inserted in the bladder, a tumor in the lower part is difficult to be detected and the lower part is a part where some of a tumor tends to remain after excision. Therefore, treatment using a light treatment system in combination with a TUR-Bt is desired for lower parts of bladders.

Light irradiation time is limited in application of a light treatment system to treatment of a bladder. If the light irradiation time is long, urine accumulates in the bladder during the irradiation. Because urine is colored, when urine accumulates in the bladder, the intensity of light the bladder is irradiated with is decreased and the effectiveness of the treatment is thus reduced. Therefore, the light irradiation time needs to be short and is desirably 30 minutes or less.

According to an article titled "Experimental Research on Whole Bladder Wall Photodynamic Therapy Using Scattering Medium", by Tadao Uchibayashi, et al., in Japanese Journal of Urology, May 1988, Vol. 79, No. 5, at pp. 807-813, the process of light treatment includes: dilating a bladder by filling a balloon catheter with 200 ml of an aqueous solution; and thereafter placing a light treatment probe in the center of the balloon catheter and irradiating the bladder with treatment light. If the bladder is assumed to be a sphere having a volume of 200 ml, the radius of the bladder is 3.6 cm and the surface area of the irradiated surface, that is, the surface area of the sphere is 162 $cm^2$.

Furthermore, Toshimitsu Misaki, et al. describe in an article titled "Photodynamic laser treatment of Bladder Tumors", in Acta Urologica Japonica, December 1986, Vol. 32, No. 12, at pp. 1941-1948 that irradiation energy of 100 $J/cm^2$ is needed for laser light used in photodynamic laser treatment. In this case, for an irradiation time of 30 minutes, high power treatment laser light having a total power of 100 $[J/cm^2] \times 162\ [cm^2]/30 \times 60\ [sec] = 9\ [W]$ is needed as treatment light emitted from a light treatment probe.

SUMMARY

In some embodiments, a light treatment system includes: a probe configured to be inserted into a bladder, the probe including an optical fiber configured to propagate light, and a light emitter that is provided at a distal end of the optical fiber, the light emitter being configured to emit the light; and a balloon catheter into which the probe is inserted, the balloon catheter being configured to be inserted into the bladder, the balloon catheter including a distal end portion that is to be dilated in the bladder, a wall configured to divide inside of the distal end portion into two regions, and a reflector configured to reflect the light emitted by the light emitter, the reflector being provided on a surface of the wall, the surface facing a region of the two regions, the region being where the light emitter is positioned.

In some embodiments, a light treatment system includes: a probe configured to be inserted into a bladder, the probe including an optical fiber configured to propagate light, and a light emitter that is provided at a distal end of the optical fiber, the light emitter being configured to emit the light; a balloon catheter to which the probe is inserted, the balloon catheter being configured to be inserted into the bladder, the balloon catheter including a distal end portion that is to be dilated in the bladder; and a wall configured to divide inside of the distal end portion into two regions, the wall having a total reflection surface facing a region of the two regions, the region being opposite to another region of the two regions, the other region being where the light emitter is positioned; and a liquid including light scattering particles and filling the other region of the two regions, the other region being where the light emitter is positioned.

In some embodiments, provided is a balloon catheter into which a probe is inserted and that is to be inserted into a bladder. The probe includes an optical fiber configured to propagate light, and a light emitter that is provided at a distal end of the optical fiber, the light emitter is configured to emit the light. The balloon catheter includes: a distal end portion that is to be dilated in the bladder; a wall configured to divide inside of the distal end portion into two regions; and a reflector configured to reflect the light emitted by the light emitter, the reflector being provided on a surface of the wall, the surface facing a region of the two regions, the region being where the light emitter is positioned.

The above and other features, advantages and technical and industrial significance of this disclosure will be better understood by reading the following detailed description of presently preferred embodiments of the disclosure, when considered in connection with the accompanying drawings.

DETAILED DESCRIPTION

Modes for implementing the disclosure (hereinafter, referred to as "embodiments") will be described below by reference to the appended drawings.

First Embodiment

Figure 1:
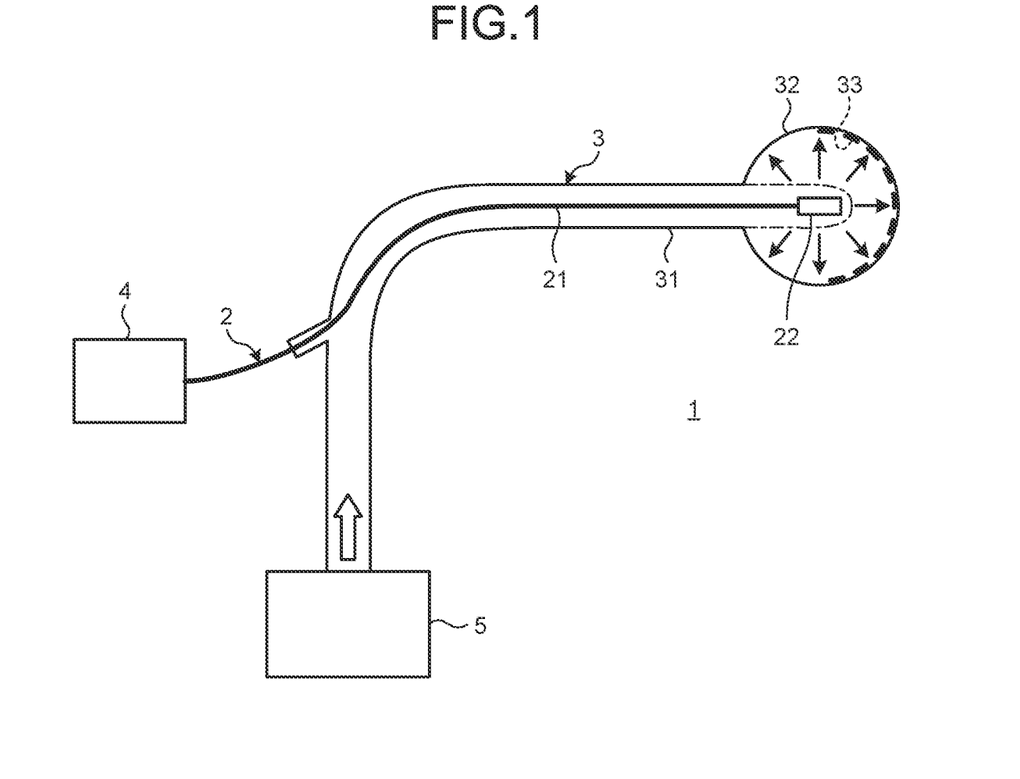
FIG. 1 is a diagram illustrating a configuration of main parts of a light treatment system according to a first embodiment.

FIG. 1 is a diagram illustrating a configuration of main parts of a light treatment system according to a first embodiment. A light treatment system 1 illustrated in FIG. 1 is a system for treating a bladder by using light.

The light treatment system 1 includes a probe 2, a balloon catheter 3, a light source device 4, and an air generating device 5.

The probe 2 includes: an optical fiber 21 that is made of glass or plastic and propagates light for treatment; and a light emitter 22 that is provided at a distal end of the optical fiber 21, emits laser light propagated through the optical fiber 21, and is cylindrical. The light emitter 22 has a diffusing function of emitting light in all directions by scattering light. Power of laser light emitted by the light emitter 22 may be at conventional low power of about 40% to 60%. The probe 2 is flexible and is able to be inserted into the bladder via the urethra of a human body.

The balloon catheter 3 includes: a main body 31 through which the probe 2 is able to be inserted; a distal end portion 32 that is provided at a distal end of the main body 31 and is spherically dilatable in a bladder; and a reflector 33 that is provided on an inner surface of the distal end portion 32 and reflects light emitted by the light emitter 22. The reflector 33 is higher in reflectivity than the inner surface of the distal end portion 32. By the distal end portion 32 reaching a bladder and dilating therein, position of the distal end portion 32 inside the bladder is fixed. The light emitter 22 of the probe 2 reaches the inside of the distal end portion 32, and by the distal end portion 32 being fixed in the bladder, position of the probe 2 in the bladder is fixed. The reflector 33 is a flexible film stuck on a rear surface of the distal end portion 32, the flexible film having a mirror coating formed by sputtering. The main body 31 is made of a material that is thin, elastic, and transparent. This material may be, for example, natural rubber, silicone rubber, or thermoplastic elastomer. While reflectivity of natural rubber is 10% to 20%, an example of the reflector 33 has reflectivity of 80% to 85%. This example is a flexible film stuck on natural rubber, the flexible film having been mirror-coated with aluminum oxide by sputtering.

The light source device 4 generates light to be supplied to an end surface of the optical fiber 21, the end surface being at a proximal end of the optical fiber 21.

Light generated by the light source device 4 is, for example, laser light.

The air generating device 5 dilates the distal end portion 32 by sending air at a predetermined pressure into the balloon catheter 3.

Figure 2:
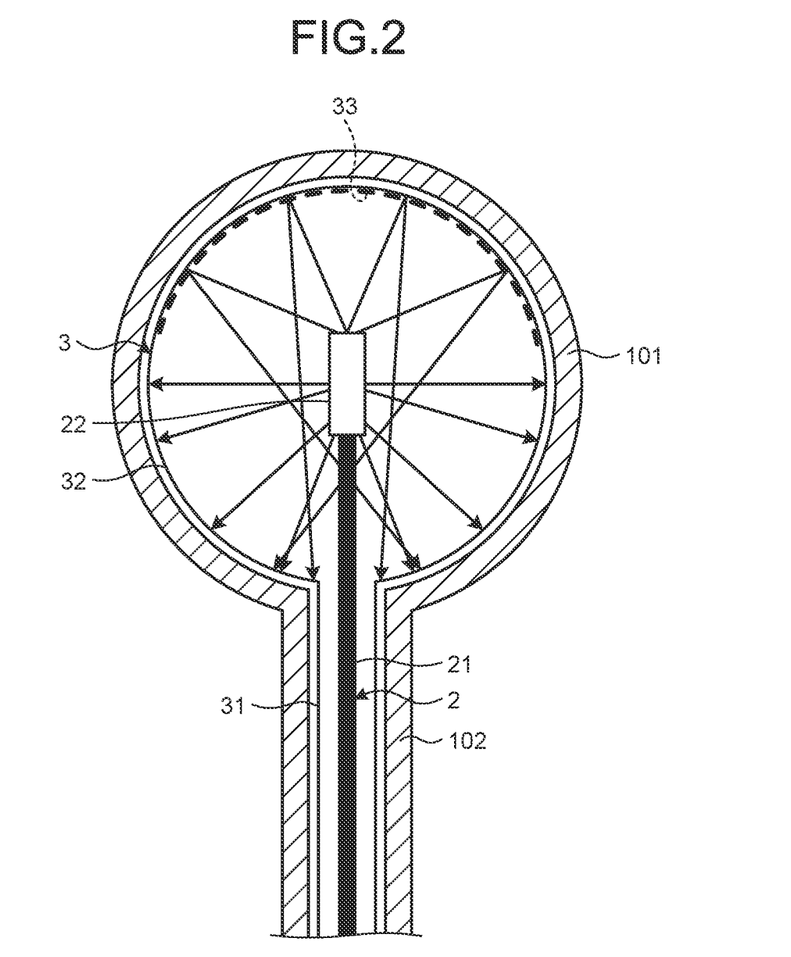
FIG. 2 is a diagram illustrating a state where light treatment is being performed by insertion of the light treatment system according to the first embodiment into a bladder.

FIG. 2 is a diagram illustrating a state where light treatment is being performed by insertion of the light treatment system 1 having the above configuration into a bladder 101. In performing treatment in the state illustrated in FIG. 2, the balloon catheter 3 is inserted into the bladder 101 from a urethra 102, the probe 2 is thereafter inserted into the balloon catheter 3, air is supplied to the distal end portion 32 of the balloon catheter 3, and the distal end portion 32 is thereby dilated and fixed in the bladder 101. Thereafter, power of the light source device 4 is turned on to cause the light source device 4 to generate light for treatment. The light emitter 22 of the probe 2 irradiates inside of the bladder 101 with the light generated by the light source device 4 and propagated through the optical fiber 21.

In the state illustrated in FIG. 2, light emitted by the light emitter 22 directly reaches the lower part in FIG. 2, that is, the periphery of the prostate, the periphery being in the vicinity of a boundary between the urethra 102 and the bladder 101. Furthermore, light emitted to the upper part in FIG. 2, that is, an upper part of the bladder, is reflected by the reflector 33, heads downward in FIG. 2, and illuminates a lesion around the prostate. Therefore, the lesion around the prostate is able to be directly and indirectly irradiated with light and efficiently treated.

According to the first embodiment described above, treatment light is reflected by a reflector provided at a distal end portion of a balloon catheter and emitted to a lower part of a bladder intently, and thus even if treatment light incident on the optical fiber is comparatively low in power, treatment effects are able to be obtained.

Furthermore, according to the first embodiment, because treatment light is emitted to the lower part of the bladder where a tumor is difficult to be excised with a rigid endoscope and some of the tumor tends to remain, the whole bladder is able to be treated evenly using the irradiation in combination with a rigid endoscope.

Second Embodiment

Figure 3:
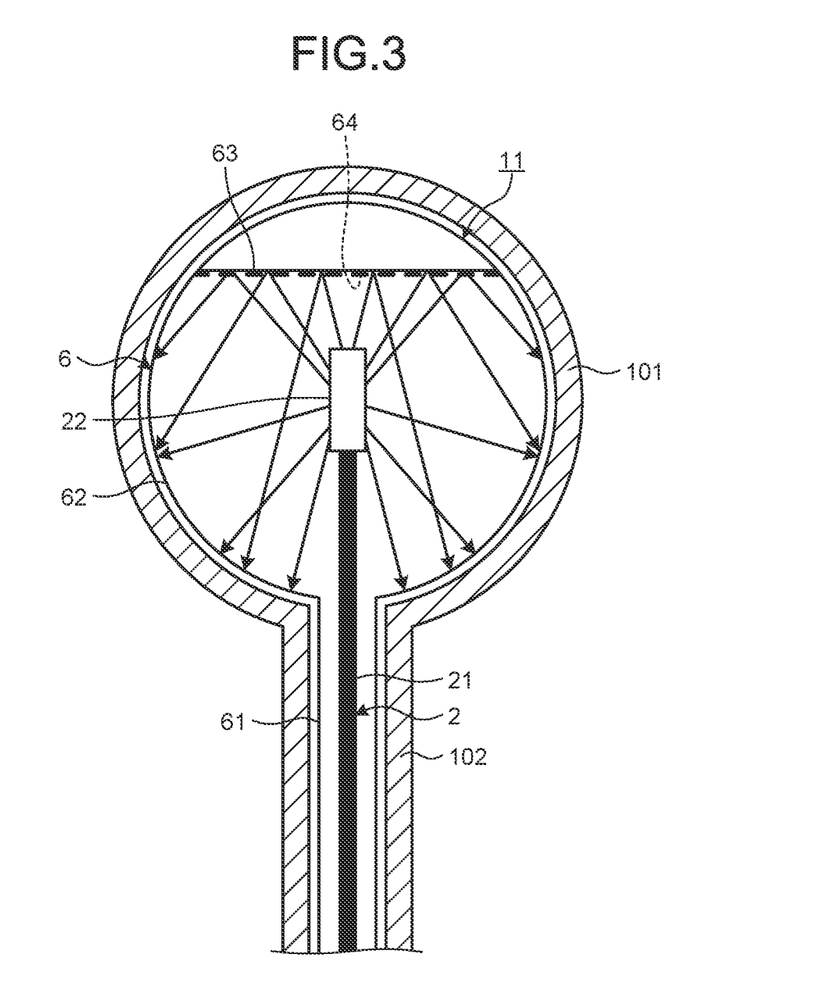
FIG. 3 is a diagram illustrating a state where light treatment is being performed by insertion of a light treatment system according to a second embodiment into a bladder.

FIG. 3 is a diagram illustrating a configuration of main parts of a light treatment system according to a second embodiment. FIG. 3 illustrates a state where light treatment is being performed by insertion of a light treatment system 11 into the bladder 101, similarly to FIG. 2. Elements having the same configurations as those of the first embodiment will be described below using the same reference signs as the first embodiment.

The light treatment system 11 includes: the probe 2; and a balloon catheter 6 in which the probe 2 has been inserted and which includes a distal end portion that dilates inside a bladder.

The balloon catheter 6 includes: a main body 61 through which the probe 2 is able to be inserted; a distal end portion 62 that is able to be dilated inside the bladder 101; a wall 63 that is provided inside the distal end portion 62 and divides the distal end portion 62 into two regions; and a reflector 64 that is provided on a surface of the wall 63, the surface facing the probe 2, and reflects light emitted by the light emitter 22. The wall 63 is approximately tabular in a state where the distal end portion 62 has been dilated (the state illustrated in FIG. 3). The reflector 64 is a flexible film with a mirror coating formed by sputtering, similarly to the reflector 33 described with respect to the first embodiment. The wall 63 may be not approximately tabular, and may form, for example, a curved surface.

When the light treatment system 11 having the above configuration is placed inside the bladder 101 and light is emitted by the light emitter 22, much of light emitted by the light emitter 22 to be diffused in all directions and reflected by a reflecting surface heads to a lateral surface because the reflecting surface is planar.

According to the second embodiment described above, treatment light is reflected by a reflector provided on a wall included in a distal end portion of a balloon catheter and emitted to the lower part of a bladder intently, and thus even if the treatment light is low in power, treatment effects are able to be obtained, similarly to the first embodiment.

Furthermore, according to the second embodiment, because treatment light is reflected by the reflector provided in the distal end portion of the balloon catheter and emitted to the lower part of the bladder intently, the lower part and lateral part of the bladder are able to be illuminated efficiently.

Third Embodiment

Figure 4:
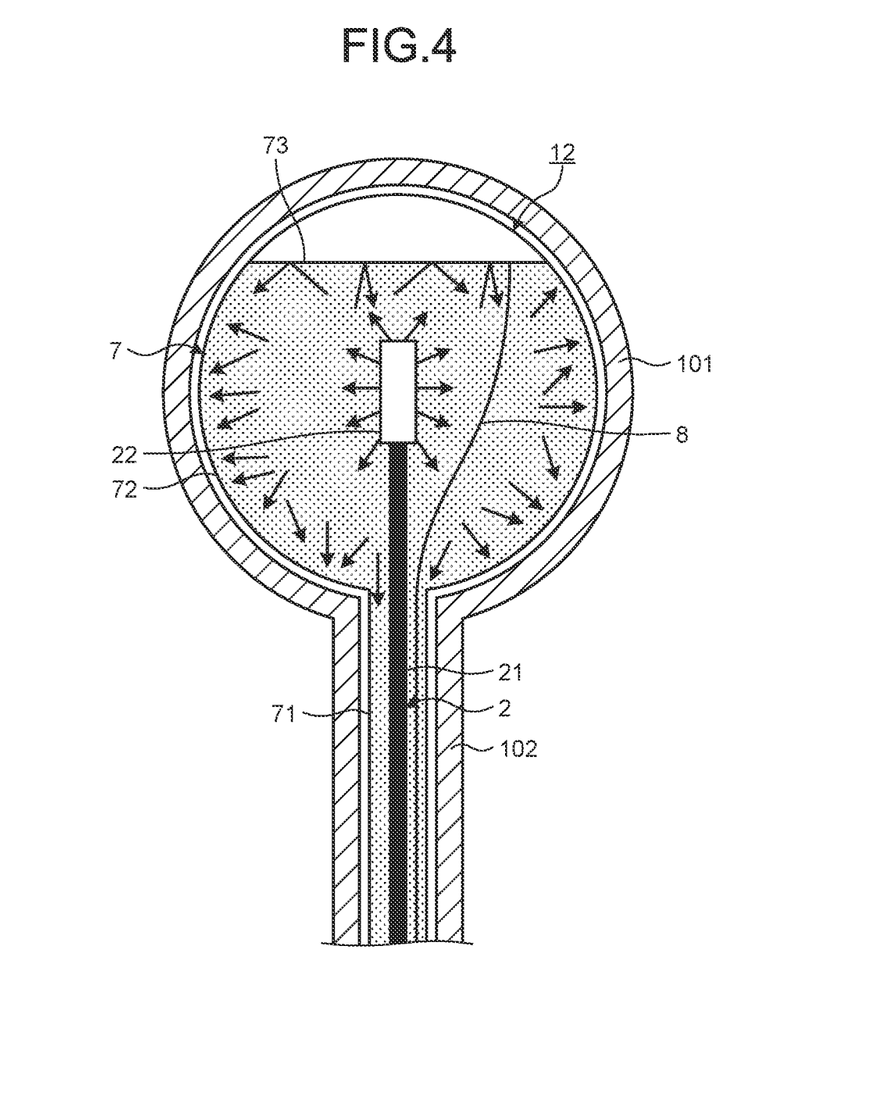
FIG. 4 is a diagram illustrating a state where light treatment is being performed by insertion of a light treatment system according to a third embodiment into a bladder.

FIG. 4 is a diagram illustrating a configuration of main parts of a light treatment system according to a third embodiment. FIG. 4 illustrates a state where light treatment is being performed by insertion of a light treatment system 12 into the bladder 101, similarly to FIG. 1. Elements having the same configurations as those of the first embodiment will be described below using the same reference signs as the first embodiment.

The light treatment system 12 includes: the probe 2; a balloon catheter 7 in which the probe 2 has been inserted and which includes a distal end portion that dilates inside a bladder; and a flow channel 8 through which air is sent to the distal end portion of the balloon catheter 7.

The balloon catheter 7 includes: a main body 71 through which the probe 2 is able to be inserted; a distal end portion 72 that is able to be dilated inside the bladder; and a wall 73 that is provided inside the distal end portion 72 and divides the distal end portion 72 into two regions. The wall 73 is approximately tabular in a state where the distal end portion 72 has been dilated. In this third embodiment also, the wall 73 may be not approximately tabular, and may form, for example, a curved surface.

When this light treatment system 12 is used by being inserted into the bladder 101, the distal end portion 72 of the balloon catheter 7 is dilated in a bladder, and a region of the regions partitioned by the wall 73 is filled with a liquid including light scattering particles, the region including the probe 2. Furthermore, air is sent, via the flow channel 8, into a region of the regions partitioned by the wall 73, the region not including the probe 2. The distal end portion 72 is thereby dilated inside the bladder 101 and fixed in the bladder 101.

The liquid including the light scattering particles is, for example, a liquid having a fat emulsion serving as the light scattering particles, the fat emulsion having been diluted with a physiological saline solution. Furthermore, the liquid including the light scattering particles may be a liquid having plastic microbeads serving as the light scattering particles, the plastic microbeads having been diluted with water. More generally, when the solvent is water, the light scattering particles are preferably made of a material comparatively low in light absorptivity, having specific gravity similar to that of water, and having a refractive index different from that of water by a predetermined standard or more. The solvent may be an aqueous solution of a surfactant or an aqueous solution of glycerol, the aqueous solution having water as the main constituent. If the solvent is an aqueous solution of a surfactant, aggregation of the light scattering particles is able to be prevented. Furthermore, if the solvent is an aqueous solution of glycerol, sedimentation velocity of the light scattering particles is able to be decreased by increase in viscosity of the liquid.

In the light treatment system 12 having the above configuration, the region of the two regions partitioned by the wall 73 is filled with liquid, the region being where the probe 2 has been placed (the lower region in FIG. 4), and the other region (the upper region in FIG. 4) is filled with air. Therefore, rays of light incident on the wall 73 at an angle larger than a critical angle are totally reflected by a surface (the upper surface in FIG. 4) of the wall 73 facing the region filled with air. For example, if the wall 73 is made of polyethylene, its refractive index is 1.54 and the critical angle is $40°(=\sin^{-1}(1/1.54))$. Therefore, the proportion of rays of light that are totally reflected is $76\%(=\cos 40°)$ and most of the light is thus able to be reflected.

Furthermore, the light scattering particles included in the liquid cause multiple scattering and a surface of the bladder wall in contact with the distal end portion 72 is thus illuminated at uniform brightness.

According to the third embodiment described above, because a wall is provided in a distal end portion of a balloon catheter and a region including a light emitter is filled with an aqueous solution including light scattering particles; multiple scattering of light emitted by the light emitter occurs in the region, and similarly to the first embodiment, even if the treatment light is low in power, treatment effects are able to be obtained.

Furthermore, according to the third embodiment, as a result of the multiple scattering, light is able to evenly reach, in addition to the lower part and lateral part of the bladder, the vicinity of the boundary between the bladder 101 and urethra 102, and thus the vicinity of the boundary between the bladder 101 and urethra 102 where light is difficult to reach is also able to be treated.

Fourth Embodiment

Figure 5:
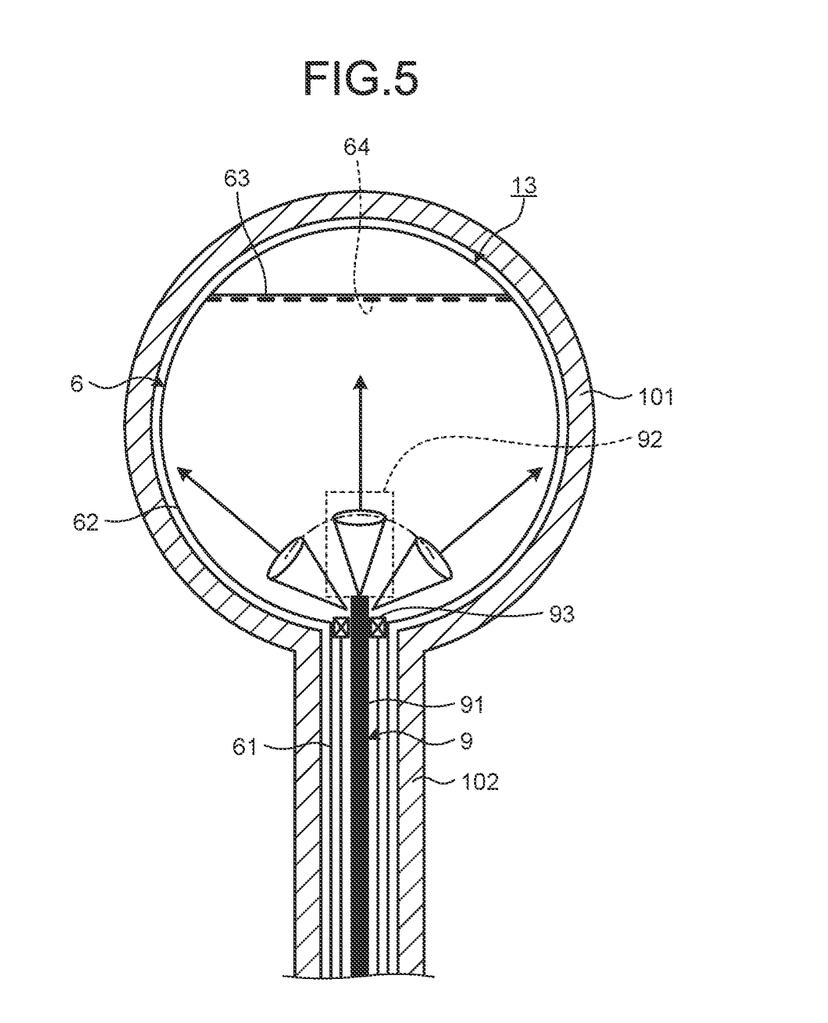
FIG. 5 is a diagram illustrating a state where light treatment is being performed by insertion of a light treatment system according to a fourth embodiment into a bladder.

FIG. 5 is a diagram illustrating a configuration of main parts of a light treatment system according to a fourth embodiment. FIG. 5 illustrates a state where light treatment is being performed by insertion of a light treatment system 13 into the bladder 101, similarly to FIG. 1. Elements having the same configurations as those of the first embodiment will be described below using the same reference signs as the first embodiment.

The light treatment system 13 includes: a probe 9 that is able to be inserted into the bladder 101 and emits light for treatment from a distal end of the probe 9; and the balloon catheter 6 where the probe 9 has been inserted, the balloon catheter 6 having a distal end portion that dilates in the bladder.

The probe 9 includes: an optical fiber 91 that propagates light for treatment; a light emitter 92 that is provided at a distal end of the optical fiber 91 and emits light propagated through the optical fiber 91 over a wide angle; and an actuator 93 that drives the light emitter 92 and changes the direction of emission. The light emitter 92 is formed of a wide-angle lens that enables light to be emitted over a wide angle range of about 120°. The actuator 93 is formed using, for example, an electromagnet or a piezoelectric element, and drives the light emitter 92 to change the direction of emission by the light emitter 92. The actuator 93 turns the light emitter 92, for example, in each of planes that are orthogonal to each other.

When the light treatment system 13 having the above configuration is placed in the bladder 101 and the light emitter 92 emits light, the actuator 93 slants the direction of emission by the light emitter 92 and a lateral surface of the bladder 101 is thus able to be illuminated. The inner surface of the bladder 101 is able to be evenly irradiated with the light emitted to the lateral surface and light reflected by the reflector 64 of the balloon catheter 6, the inner surface being from the lateral surface to the lower part of the bladder 101.

According to the fourth embodiment described above, since the direction of emission of light is changed in a bladder by driving a light emitter using an actuator, treatment effects are able to be obtained even if the treatment light is low in power, similarly to first embodiment.

Furthermore, according to the fourth embodiment, since illumination with light is performed using a wide-angle illumination lens, all of rays of treatment light passing through the lens illuminate the inner wall of the bladder. Therefore, loss of the treatment light is able to be reduced even further.

Other Embodiments

Modes for carrying out the disclosure have been described above, but the disclosure is not to be limited only to the above described first to fourth embodiments. For example, a light emitter may be spherical, or may have a front-emitting form not having a diffusing function.

Therefore, the disclosure may include various embodiments not described herein.

According to the disclosure, treatment effects are able to be obtained even if treatment light is low in power.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light treatment system, comprising:
a probe comprising:
an optical fiber configured to propagate light, and
a light emitter provided at a distal end of the optical fiber, the light emitter being configured to emit the light; and
a balloon catheter into which the probe is inserted, the balloon catheter being configured to be inserted into the bladder, the balloon catheter comprising:
a balloon configured to be dilated in the bladder, the balloon being configured to accommodate the light emitter in an interior cavity of the balloon,
a wall configured to divide the interior cavity of the balloon into first and second regions, the first and second regions being separate from each other, the first region being configured to hold a first fluid to dilate the balloon; and
a reflector configured to reflect the light emitted by the light emitter, the reflector being provided on a surface of the wall, the surface facing the first region, the light emitter being accommodated within the first region.

2. The light treatment system according to claim 1, wherein the reflector is higher in reflectivity than an inner surface of the balloon.

3. The light treatment system according to claim 1, wherein the reflector is provided along a part of an inner surface of the balloon.

4. A light treatment system, comprising:
a probe comprising:
an optical fiber configured to propagate light, and
a light emitter provided at a distal end of the optical fiber, the light emitter being configured to emit the light;
a balloon catheter being configured to be inserted into the bladder, the balloon catheter comprising:
a balloon configured to be dilated in the bladder, the balloon being configured to accommodate the light emitter in an interior cavity of the balloon; and
a wall configured to divide the interior cavity of the balloon into first and second regions,
wherein the first and second regions being separate from each other such that the first region is configured to hold a liquid, the liquid including light scattering particles and a second region being configured to hold a fluid, the fluid being different from the liquid such that the wall having a total reflection surface facing the first region, the first region being opposite to the second region; and
the light emitter being accommodated within the first region.

5. A balloon catheter comprising:
a main body into which a probe is inserted, the main body being configured to be inserted into a bladder, the probe including an optical fiber configured to propagate light, and a light emitter provided at a distal end of the optical fiber, the light emitter being configured to emit the light, the balloon catheter comprising:
a balloon configured to be dilated in the bladder, the balloon being configured to accommodate the light emitter in an interior cavity of the balloon;
a wall configured to divide the interior cavity of the balloon into first and second regions, the first and second regions being separate from each other, the first region being configured to hold a first fluid to dilate the balloon; and
a reflector configured to reflect the light emitted by the light emitter, the reflector being provided on a surface of the wall, the surface facing the first region, the light emitter being accommodated within the first region.

* * * * *